United States Patent
Cooper et al.

[11] Patent Number: 5,792,196
[45] Date of Patent: Aug. 11, 1998

[54] RATE-RESPONSIVE PACEMAKER WITH AUTOMATIC RATE RESPONSE FACTOR SELECTION

[76] Inventors: Daniel Cooper, 17 Rue Schilling, 67500 Hauguenau, France; Dean J. MacCarter, 5884 S. Macon, Englewood, Colo. 80111

[21] Appl. No.: 823,077

[22] Filed: Mar. 24, 1997

Related U.S. Application Data

[63] Continuation of Ser. No. 641,223, Apr. 30, 1996, abandoned.

[51] Int. Cl.$^6$ .................................................. A01N 1/36
[52] U.S. Cl. ........................... 607/17; 607/19; 607/20
[58] Field of Search ............................ 607/17, 19, 20

[56] References Cited

U.S. PATENT DOCUMENTS

| | | | |
|---|---|---|---|
| 4,596,251 | 6/1986 | Plicchi et al. | 607/20 |
| 4,856,522 | 8/1989 | Hansen | 607/17 |
| 4,901,725 | 2/1990 | Nappholz et al. | 607/17 |
| 5,085,215 | 2/1992 | Nappholz et al. | 607/17 |
| 5,282,839 | 2/1994 | Roline et al. | 607/19 |
| 5,292,340 | 3/1994 | Crosby et al. | 607/17 |
| 5,383,473 | 1/1995 | Moberg . | |
| 5,441,523 | 8/1995 | Nappholz | 607/14 |
| 5,487,753 | 1/1996 | MacCarter et al. . | |
| 5,562,711 | 10/1996 | Yerich et al. | 607/17 |
| 5,609,610 | 3/1997 | Nappholz . | |
| 5,690,687 | 11/1997 | Hansen | 607/17 |

FOREIGN PATENT DOCUMENTS

9320889  10/1993  European Pat. Off. .

*Primary Examiner*—William E. Kamm
*Assistant Examiner*—Carl H. Layno
*Attorney, Agent, or Firm*—Gottlieb, Rackman & Reisman

[57] ABSTRACT

A rate responsive pacemaker senses an instantaneous metabolic indicative parameter such as minute volume and monitors this parameter over an extended time period of 30 days. A corresponding cumulative rate control parameter is generated. The cumulative rate parameter is converted into a metabolic pulsing rate for generating pulses in accordance with a set of physical activity parameters.

17 Claims, 10 Drawing Sheets

RATE-RESPONSIVE PACEMAKER WITH AUTOMATIC RATE RESPONSE FACTOR SELECTION

RELATED APPLICATIONS

This is a continuation of application Ser. No. 08/641,223 filed Apr. 30, 1996, now abandoned.

BACKGROUND OF THE INVENTION

1. Field of the Invention

This invention relates to rate-responsive pacemakers and, more particularly, to pacemakers that employ a metabolic demand sensor whose output is adjusted in accordance with a rate response dependent on the physical condition of a patient.

2. Description of the Prior Art

Many attempts have been made to control the heart rate of a pacemaker patient so that it will duplicate the intrinsic heart rate of a healthy person both when the patient is at rest and when the patient is involved in various levels of exercise. Metabolic demand related parameters heretofore proposed for controlling the pacing rate include the QT interval, respiration rate, venous oxygen saturation, stroke volume, venous blood temperature, and minute volume, among others. In addition, the use of mechanical and electrical sensors which detect patient motion have also been explored in such attempts at achieving improved rate-responsiveness. Of the various parameters available, it has been found that pacemakers using minute volume as a parameter for controlling pacing rate are particularly advantageous. However, a problem with these types of pacers has been the mapping of minute volume to an appropriate metabolic indicated rate in a manner which accurately reflects the intrinsic heart rate.

A further problem is that, in general, even though metabolically-related parameters used for controlling rate-responsive pacemakers react fairly rapidly in reflecting changes in the patient's physical activity, the pacemakers' algorithm does not react with the same speed or time constant. This can result in the patient having a hemodynamic deficiency due to the lag time involved between the start of an increased level of exercise and the reaction thereto by the pacemaker.

An early attempt at mapping the minute volume was to use a straight linear conversion into impulse interval, or metabolic rate interval (MRI). This mapping was found to be undesirable because it led to a hyperbolic relationship or mapping between the minute volume AMV and the metabolic indicated rate (MIR) which provided a very small response at low levels of minute volume.

Another type of mapping tried in the past was a straight linear mapping between MIR and ΔMV. This mapping while conforming more closely to the actual relationship between AMV and the intrinsic heart rate, it still did not respond sufficiently to very low minute volume levels.

Yet another mapping tried in the past was a two-slope interval-based mapping. This method closely approximated the linear-based single slope mapping and hence was inaccurate for the reasons discussed above.

In summary, a mapping using a single RRF value as a slope is unsatisfactory because it ignores the need for a faster response during the initial or exercise level, and the need for a different response at high exercise levels. A mapping in which two line segments are used and the initial slope was set to a preselected RRF is still unsatisfactory because it relies on an artificial transition or break point between the line segments.

A further problem with prior art pacemakers is that they incorporate a long term filter in the minute volume determination to determine a minute volume baseline. The filter approximates the average minute volume ventilation output which varies during extended exercise. Therefore extended exercise may result in a final value which is too low.

U.S. Pat. No. 4,856,522 discloses a pacemaker in which rate-responsive parameter values are arranged and mapped into percentile rankings.

OBJECTIVES AND SUMMARY OF THE INVENTION

In view of the above mentioned disadvantages of the prior art, it is an objective of the present invention to provide a pacemaker which dynamically responds to the changes in the physical level of activity of a patient and adjusts its mapping of the metabolic indicated rate accordingly.

A further objective is to provide a metabolic rate responsive pacemaker which generates pulses at a rate by following a profile which closely matches the profile of a healthy person, i.e., a person having no pacemaker.

Other objectives and advantages of the invention shall become apparent from the following description. Briefly, a pacemaker constructed in accordance with this invention includes sensing means for sensing a metabolic demand parameter of the patient indicative of his or her instantaneous physical activity. Preferably, the metabolic demand parameter is the minute volume which can be determined, for example, from impedance measurements. Minute volume has been found to be an accurate representation of the physical activity and the corresponding blood flow and oxygen demand of a patient. However, it should be understood that the present invention is applicable to other metabolic demand parameters as well. This parameter is used as a rate control parameter and converted into a corresponding metabolic indicated rate (MIR), which rate may be used to define the interval between the pacer pulses. The mapping of minute volume to metabolic indicated rate (MIR), preferably, uses a preselected curve which may be, for example, an exponential curve, having a slope which decreases as the minute volume increases, or other monotonic curves. Importantly, the pacemaker adjusts itself by deriving a curve and updating it dynamically by monitoring the minute volume of the patient. In this manner, the curve is modified and updated automatically to the requirement of a specific patient, and only the shape of the curve is based on information derived from statistical data from other patients.

Preferably, the rate control of the patient is monitored over a preselected time period and categorized statistically into several pre-selected percentile levels, each percentile level defining a level of physical activity. This data is then used to define a continuous linear curve used for mapping the metabolic parameter to a corresponding heart rate. The data thus obtained may also be used to define the physical fitness level of the patient and to provide a cross check for the maximum allowable pacing rate.

More specifically, a pacemaker constructed in accordance with this invention includes pulse generating means for generating pacing pulses for the patient's heart in accordance with a metabolic rate parameter; sensing means for sensing an instantaneous rate control parameter in said patient; means for generating a cumulative rate control parameter by monitoring said instantaneous rate control parameter over an extended time; determining means for determining a set of physical activity parameters from said

3 cumulative rate control parameter; and conversion means for converting said instantaneous rate control parameter into said metabolic parameter.

DETAILED DESCRIPTION OF THE INVENTION

Figure 1:
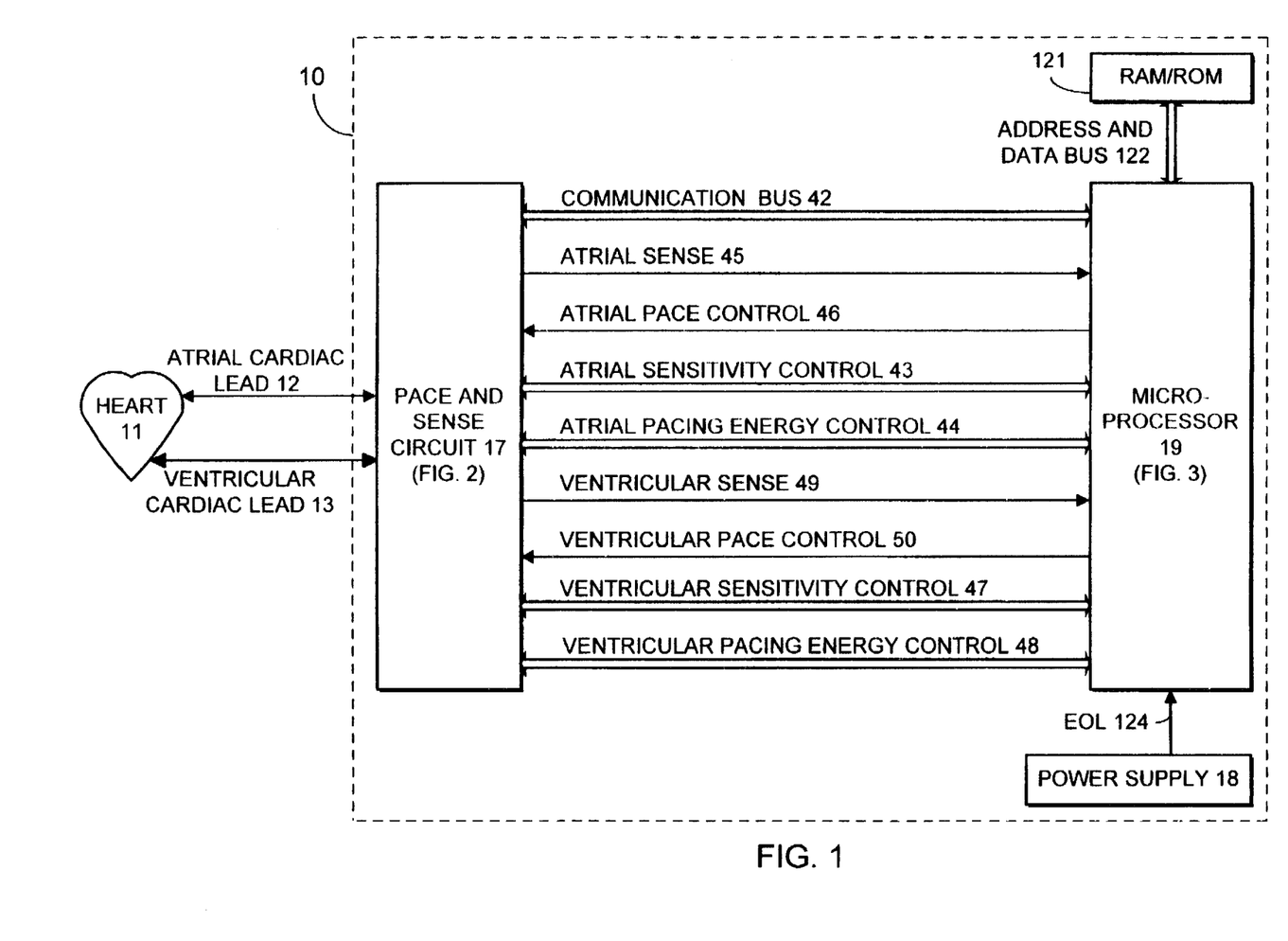
FIG. 1 shows a block diagram of a pacemaker constructed in accordance with this invention.

Studies have shown that, while the relationship between the heart rate and the minute volume is complex, it is modeled fairly accurately by a profile in the shape of a monotonic curve having a slope which decreases as the minute volume increases. Details of a pacemaker using the mono-tonic curve for mapping in accordance with this invention are shown in FIGS. 1–6. FIG. 1 shows a block diagram of the pacemaker. The pacemaker 10 is designed to be implanted in a patient and is connected by leads 12 and 13 to a patient's heart 11 for sensing and pacing the heart 11 as described for example in commonly assigned co-pending application Ser. No. 226,654, filed Apr. 12, 1994 by Tibor A. Nappholz et al., entitled "FORCED ATRIOVENTRICULAR SYNCHRONY DUAL CHAMBER PACEMAKER", now U.S. Pat. No. 5,441,523 incorporated herein by reference. Briefly, the atrial cardiac lead 12 extends into the atrium of the heart 11 and the ventricular cardiac lead 13 extends into the ventricle of the heart 11. Leads 12 and 13 are used for both sensing electrical activity in the heart and for applying pacing pulses to the heart. The pacemaker 10 includes a pace and sense circuit 17 for the detection of analog signals from leads 12 and 13 and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a voltage supply to the pace and sense circuit 17 and the microprocessor 19 by electrical conductors (not shown). The microprocessor 19 is connected to a random access memory/read only memory unit 121 by an address and data bus 122. A low power signal line 124 is used to provide to the microprocessor 19 a logic signal indicative of a low energy level of the power supply 18. The microprocessor 19 and the pace and sense circuit 17 are connected to each other by a number of data and control lines including a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 2:
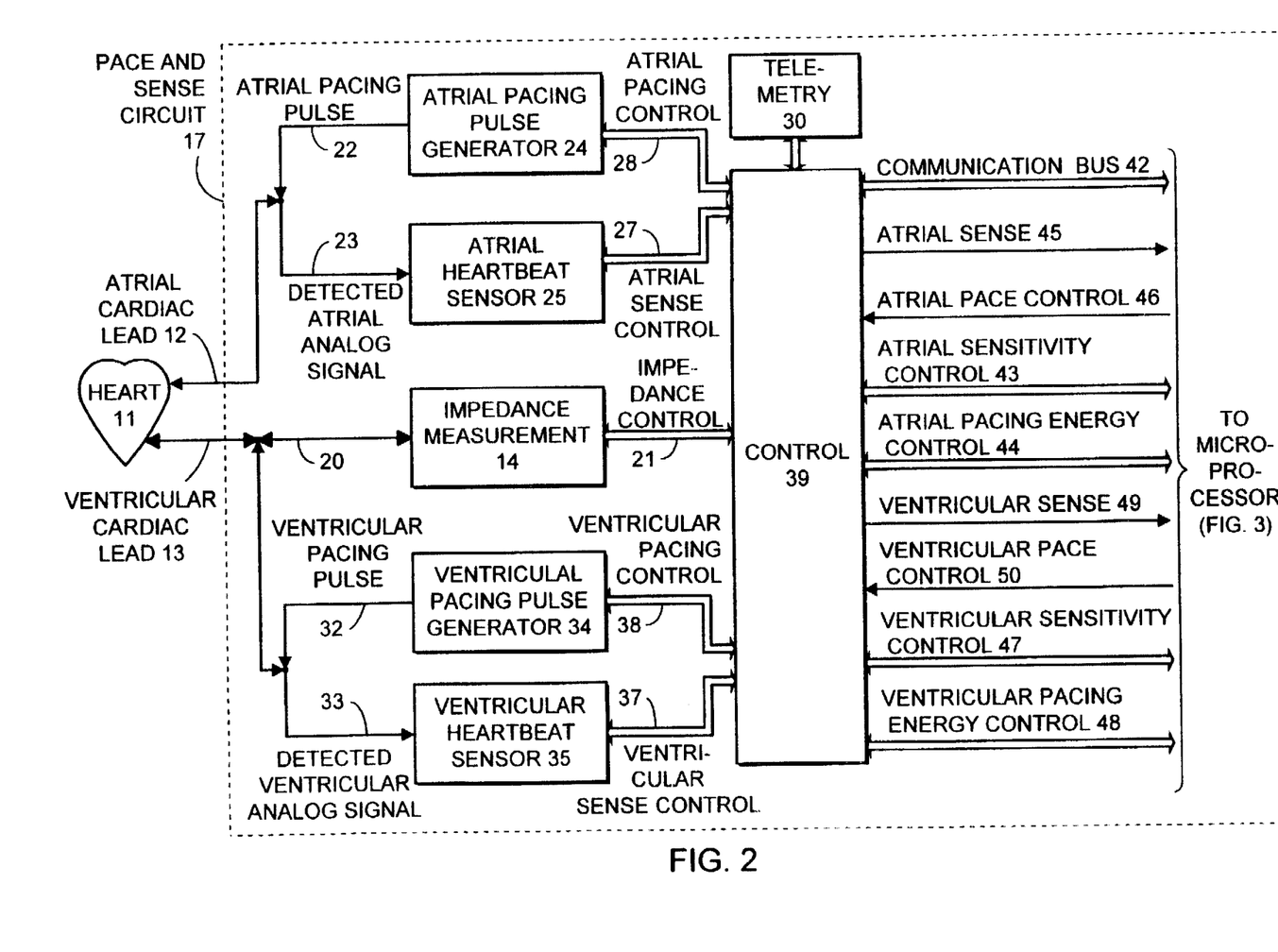
FIG. 2 shows a block diagram of the pace and sense circuit for the pacemaker of FIG. 1.

FIG. 2 shows details of the pace and sense circuit 17. The circuit 17 includes an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 also includes an impedance measurement circuit 14 for measuring a physiological parameter indicative of the patient's metabolic demand. The pace and sense circuit 17 also includes a control block 39 which is interfaced to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the sensor circuits 25 and 35 receive an input atrial sense control signal on a control bus 27 and an input ventricular sense control signal on a control bus 37, respectively, from the control block 39. These control signals are used to set the sensitivity of the respective sensors.

The atrial pacing pulse generator circuit 24 receives from the control block 39, via an atrial pacing control bus 28, an atrial pace control signal and an atrial pacing energy control signal to generate an atrial pacing pulse 22 at appropriate times. Similarly, the ventricular pacing pulse generator circuit 34 receives from the control block 39, via a ventricular pacing control bus 38, a ventricular pace control signal and a ventricular pacing energy control signal to generate a ventricular pacing pulse 32. The atrial and ventricular pace control signal determine the respective timing of atrial and ventricular pacing that take place, while the atrial and ventricular pacing energy control inputs determine the respective magnitudes of the pulse energies.

The pacemaker 10 makes an impedance measurement when the microprocessor 19 sends a signal on the impedance control bus 21 to activate the impedance measurement circuit 14. The impedance measurement circuit 14 then applies a current to the ventricular cardiac lead 13 via- lead 20 and measures a voltage resulting from the applied current. These current and voltage signals define an impedance characteristic of the patient's tidal volume. This minute volume is then estimated as the product of average tidal volume and respiratory rate, by any of several algorithms.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the 9600 Network Programmer manufactured by Telectronics Pacing Systems, Inc. of Englewood, Colo., U.S.A.

Figure 3:
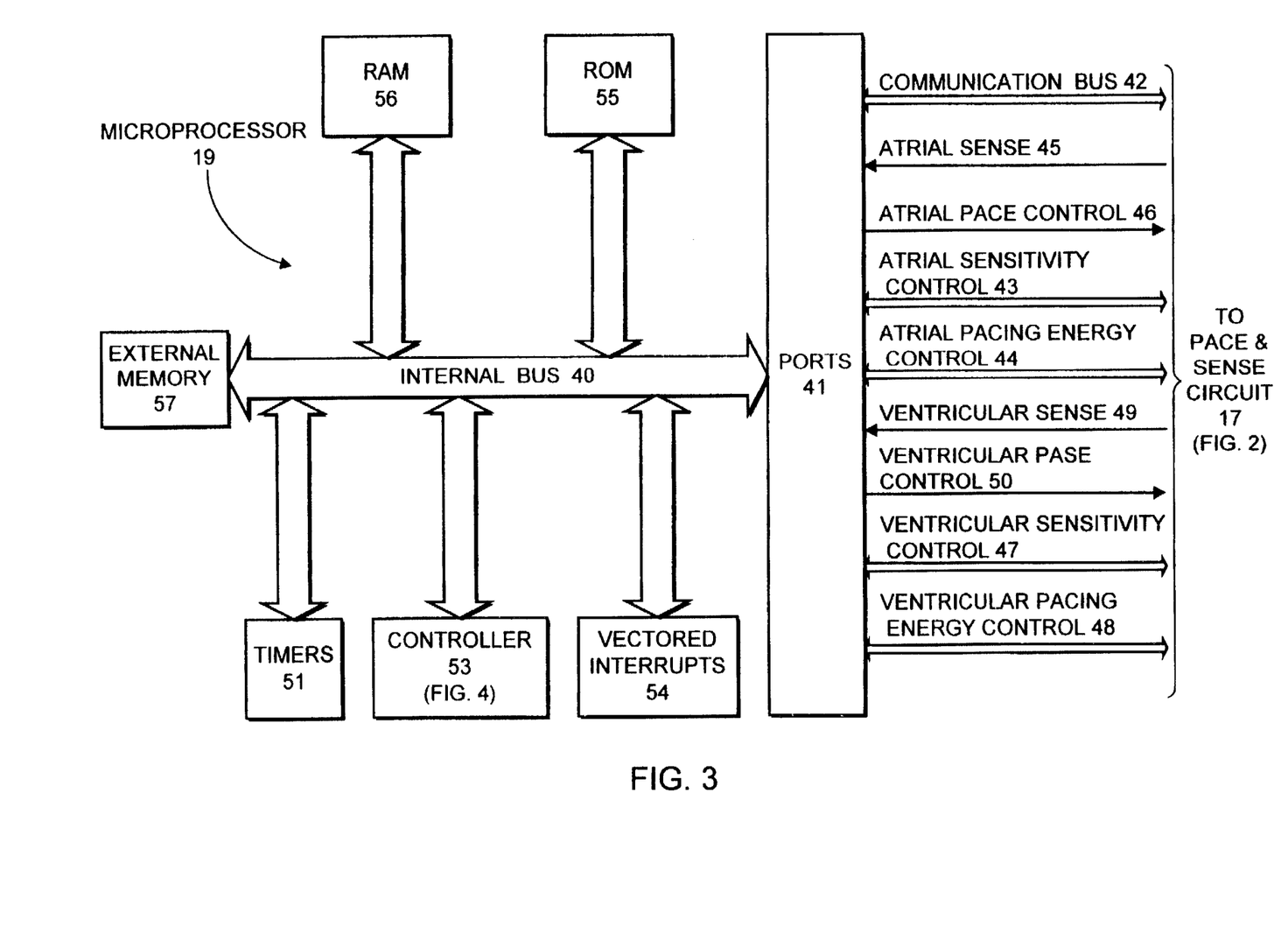
FIG. 3 shows a block diagram of a microprocessor for the pacemaker of FIG. 2.

FIG. 3 shows the microprocessor 19 having a timer circuit 51 for generating several timing signals on its output ports A–E, a controller 53, a vectored interrupts circuit 54, a ROM 55, a RAM 56, an external memory 57 and an interface port 41. Signals between these elements are exchanged via an internal communications bus 40. Timer circuits generates various timing signals. The RAM 56 acts as a scratchpad and active memory during execution of the programs stored in the ROM 55 and used by the microprocessor 19. ROM 55 is used to store programs including system supervisory programs, detection algorithms for detecting and confirming arrhythmias, and programming for determining the rate of the pacer, as well as storage programs for storing, in external memory 57, data concerning the functioning of the pulse generator 10 and the electrogram provided by the ventricular cardiac lead 13. The timer circuit 51, and its associated control software, implements some timing functions required by the microprocessor 19 without resort entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communication bus 42 serves to provide signals indicative of such control to the microprocessor 19.

The microprocessor 19 through its port 41 receives status and/or control inputs from the pace and sense circuit 17, including the sense signals on the sense lines 45 and 49 previously described. Using controller 53, it performs various operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits. The rate of the atrial and/or ventricular pacing is adjusted by controller 53 as set forth below by making use of the anaerobic threshold.

The pacemaker 10 of the present invention functions properly using any metabolic indicator rate system, so long as that system is able to reliably relate the sensed parameter to an appropriate matching of metabolic demand with the paced rate. The preferred embodiment of the invention employs the impedance measurement circuit 14, shown in FIG. 2, which measures the cardiac impedance to determine the respiratory minute volume as described in U.S. Pat. No. 4,901,725 to T. A. Nappholz, et al., issued Feb. 20, 1990 for "Minute Volume Rate-Responsive Pacemaker", incorporated herein by reference.

Figure 4:
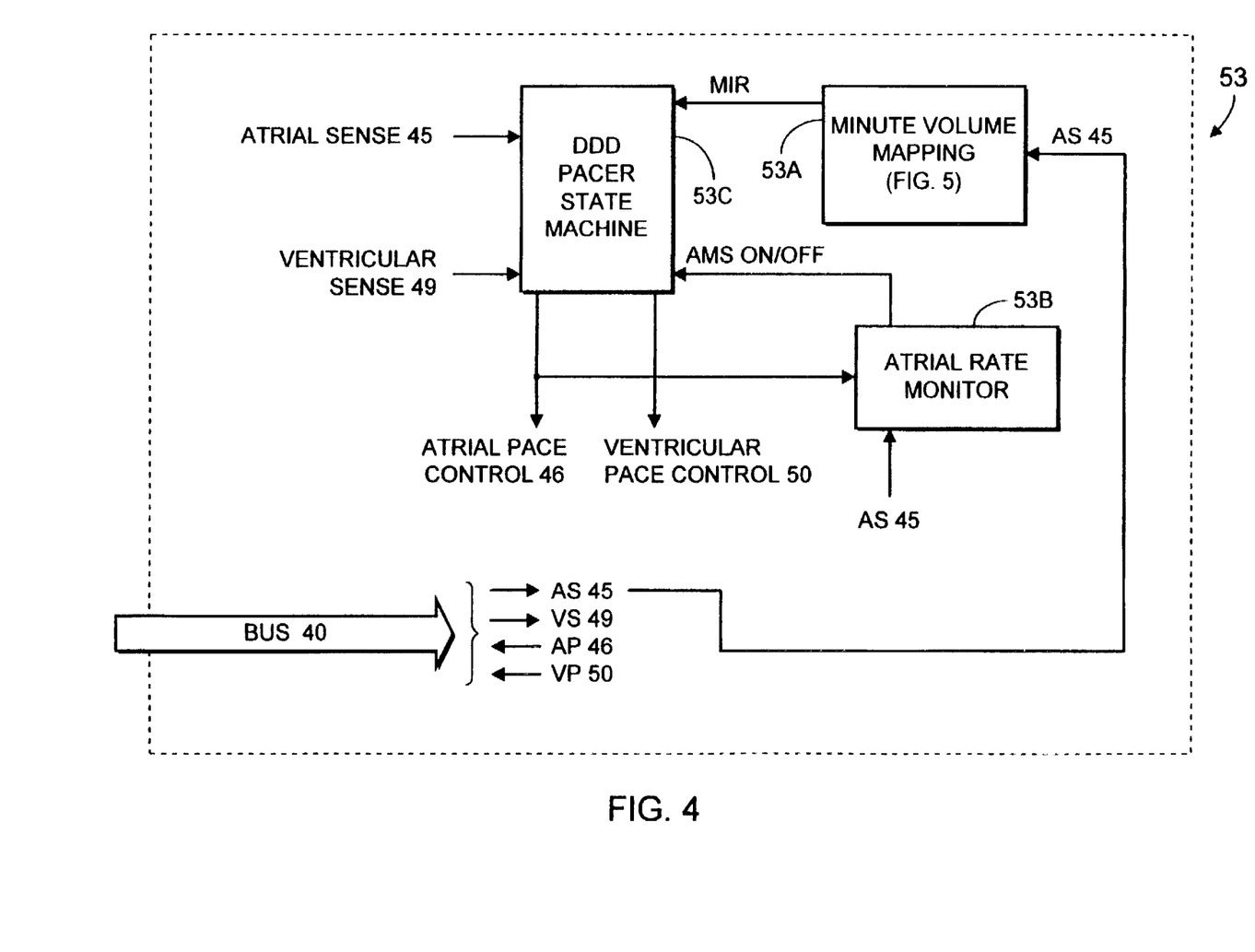
FIG. 4 shows details of the controller for the microprocessor of FIG. 3.

FIG. 4 shows the block diagram of the controller 53 of FIG. 3. The controller 53 includes a pacer 53C, which is preferably a state machine, a minute volume mapping circuit 53A and an atrial rate monitor 53B. The minute volume mapping circuit 53A uses the data supplied via the internal bus 40 and the communication bus 42 from the impedance measurement block 14 to relate the minute volume indicated by the impedance measurement to the Metabolic Indicated Rate (MIR). This rate is then used by the state machine 53C to determine the length of each interval in the timing cycle. While the pacemaker 10 is preferably operating in a DDD mode, it should be understood that it can operate in other modes as well. The atrial rate monitor 53B generates an Automatic Mode Switching (AMS) signal upon detection of a non-physiological atrial rate and rhythm. This AMS signal automatically switches the pacemaker 10 to a ventricular pacing mode, where atrial pacing is temporarily disabled. When a physiological atrial rate resumes, the AMS signal is deactivated and the pacemaker returns to an atrial tracking mode.

Figure 5:
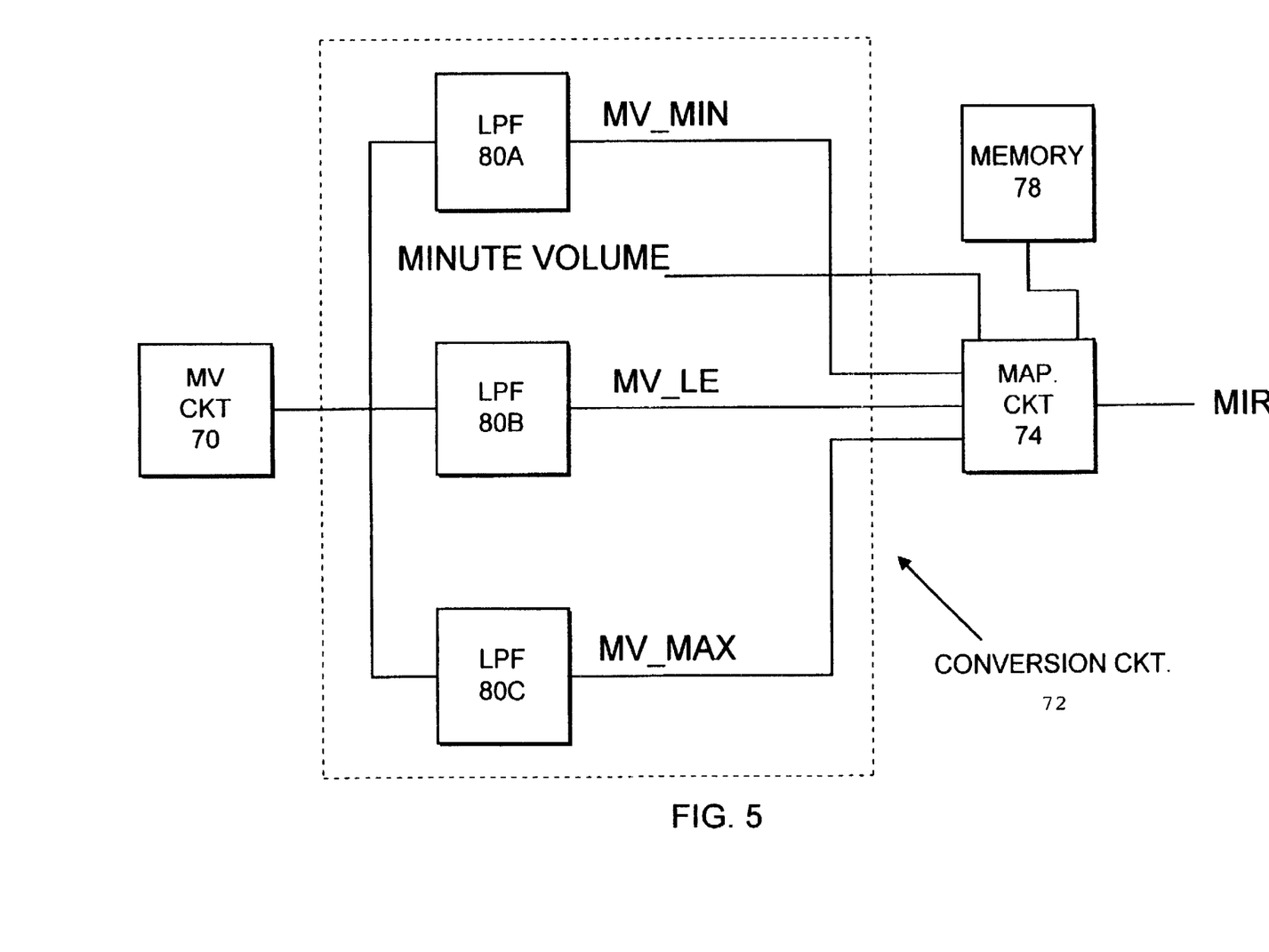
FIG. 5 shows details of the minute volume mapping circuit for the controller of FIG. 4.

Referring now to FIG. 5, the minute volume mapping circuit 53A includes a minute volume determining circuit 70 and a conversion circuit 72. Circuit 70 receives the impedance signal from impedance measurement circuit 14. The corresponding minute volume (MV) is determined by circuit 70 as described in detail in U.S. Pat. No. 4,901,725, incorporated herein by reference and is provided to the conversion circuit 72.

The conversion circuit is used to generate continuously a profile for a mapping circuit 74. The mapping circuit 74 uses this profile to generate for each received MV, a corresponding MIR parameter.

It should be understood that the conversion circuit 72 as well as the other elements of mapping circuit 53C are shown as discrete elements for the sake of clarity. However, these elements are preferably implemented by software performed, for example, by microprocessor 39.

Figure 7:
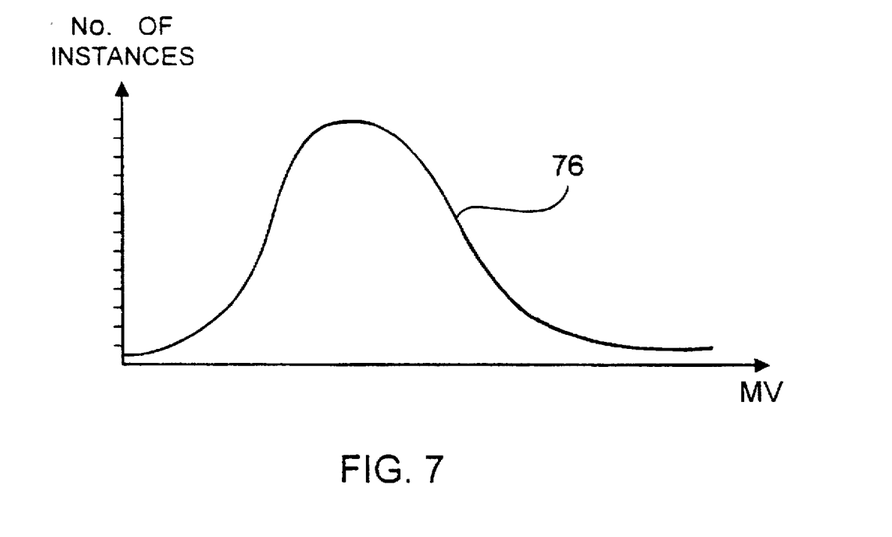
FIG. 7 shows a typical distribution of MV values for a typical patient.
Figure 8:
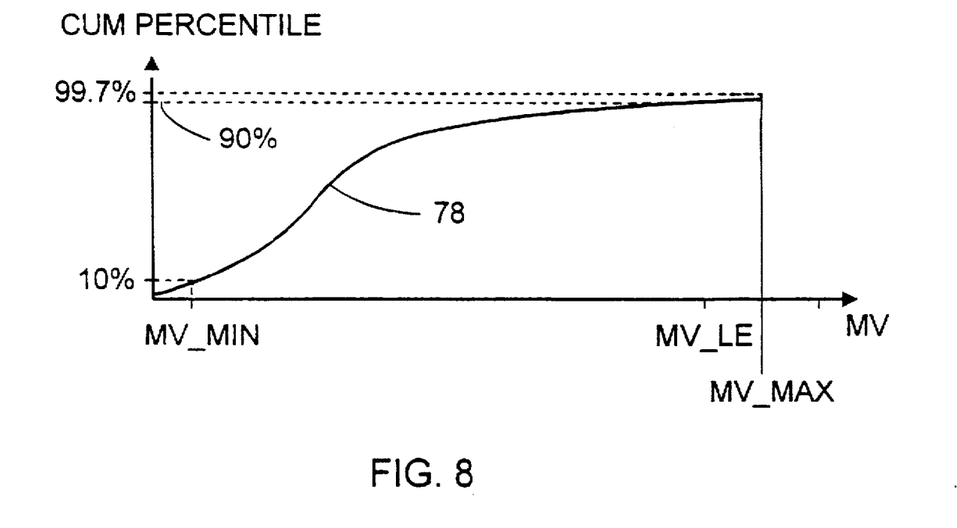
FIG. 8 shows a summation or integral for the curve of FIG. 7 for a 30 day period.

In order to provide a clear understanding of the present invention, reference is now made to FIG. 7. This Figure shows a typical bell-shaped distribution curve 76 for various values of the metabolic parameter MV as a function of their respective frequency of occurrence. FIG. 8 shows a cumulative percentile curve 78 for the curve 76 of FIG. 7. In order to obtain this curve 78, the curve 76 of FIG. 7 has been summed or integrated and normalized so that the abscissa indicates cumulative percentile. For example, the value MV_MIN is defined at the 10% cumulative percentile of MV. That is, at any given time period, 10% of the MV measurements are equal to or smaller than MV_MIN. The curves of FIGS. 7 and 8 are generated using statistical data for normal subjects. It has been found by the present inventor that the cumulative percentiles can be related to the activity level of the patient. Various cumulative percentiles values of interest are listed below:

| CUM PERCENTILE | PHYSICAL ACTIVITY | DESIGNATION |
|---|---|---|
| 10% | Sleep | MV_MIN |
| 90% | LIGHT EXERCISE | MV_LE |
| 99.7% | PEAK EXERCISE | MV_MAX |

Additional percentile values may also be used making the 50% value which corresponds to the waking rest state of a normal patient.

This information then is used in the present invention for dynamically generating the profile for converting MV to the MIR. A method and apparatus of performing this operation is now described in conjunction with the block diagram of FIG. 5, the flow chart of FIG. 6 and curves of FIGS. 7-9.

As previously mentioned, during normal operation of the pacemaker 10, MV measurements are generated at regular intervals by circuit 70. Each measurement is fed to a conversion circuit 72 which uses the MV values to generate the three parameters described above. These three parameters define a profile which can be used to translate the instantaneous MV to a corresponding MIR parameter by mapping circuit 74. Returning to FIG. 4, this MIR parameter is fed to the pacer state machine 53C which in response generates a sequence of atrial and/or ventricular pacing commands in accordance with a preselected pacing mode, such as DDD, DDDR and so on.

Figure 9:
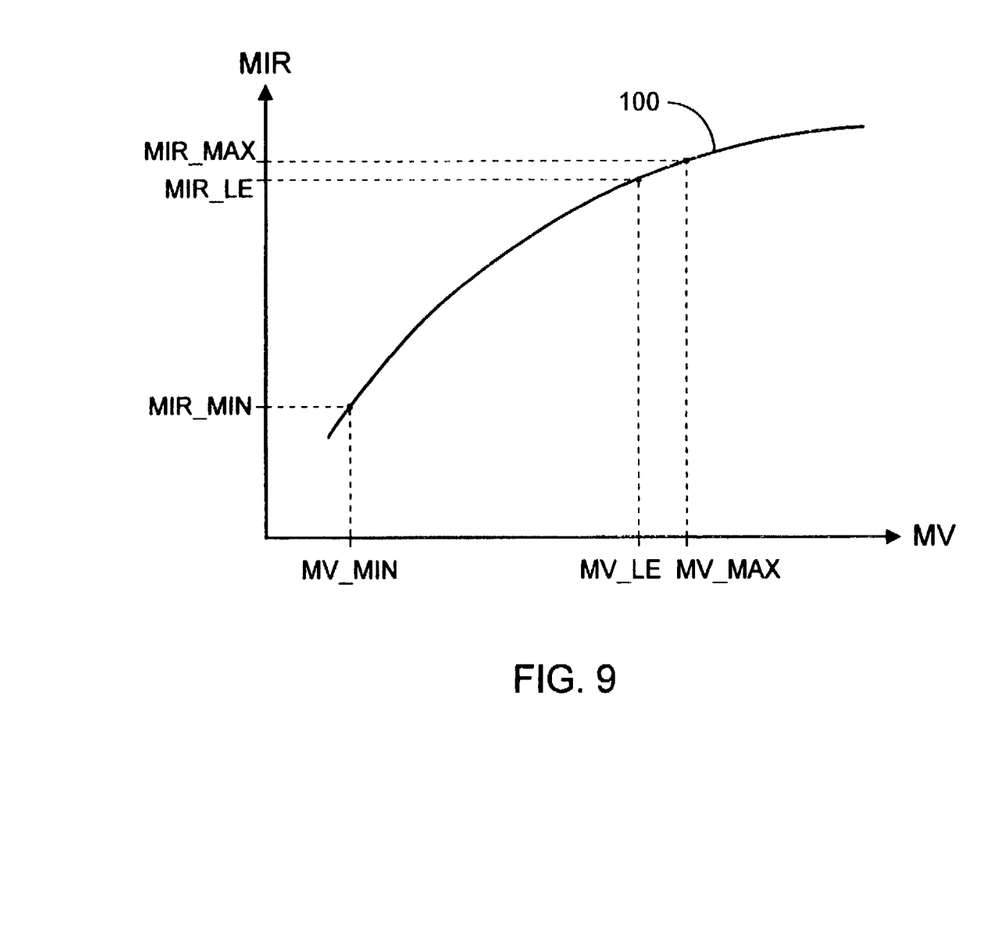
FIG. 9 shows a mapping of the minute volume to the metabolic indicated rate (MIR) in accordance with this invention.

Importantly, the conversion profile used by mapping circuit 74 is preferably a monotonic curve such as the exponential curve shown in FIG. 9. More specifically, the curve 100 in FIG. 9 is characterized by the equation:

$$MIR = a0 - a1 * \exp(-mv/a2)$$

In this equation, the coefficient a0 is a fixed asymptotic value for which a reasonable value is 230 ppm. If any two points on the curve are known, such as MV_MIN, MIR_MIN and MV_LE, MIR_LE, then the coefficients a1 and a2 can be readily obtained.

Figure 6:
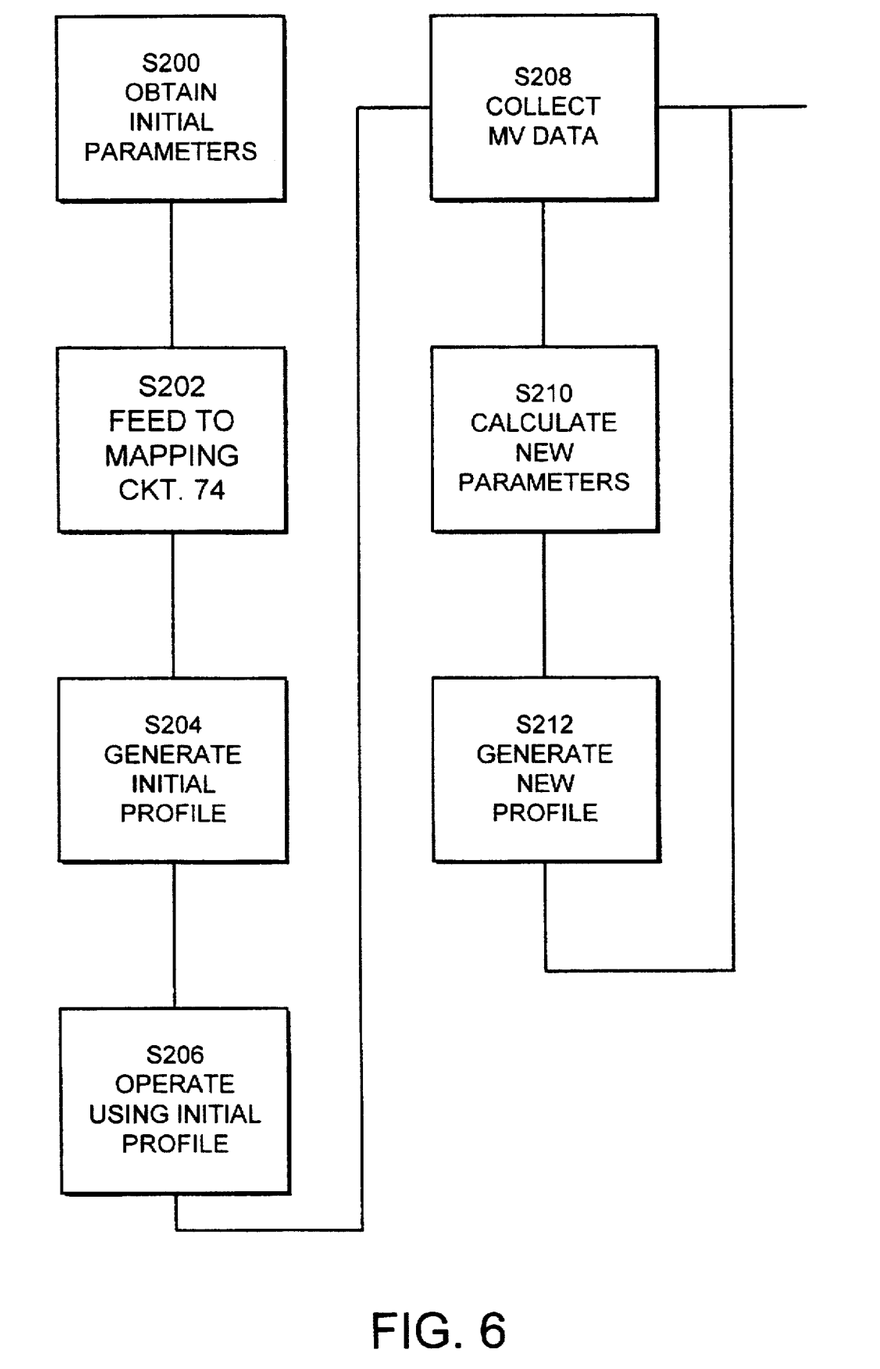
FIG. 6 shows a flow chart describing the operation of the mapping circuit of FIG. 5.

The mapping circuit 74 receives this information (Step S202), and generates the appropriate initial profile for conversion using the above formula (Step 204). The initial profile is used by the conversion circuit to generate an MIR value for each MV value received from circuit 70, either by using the formula or by using a look-up table stored in memory 78.

Figure 5A:
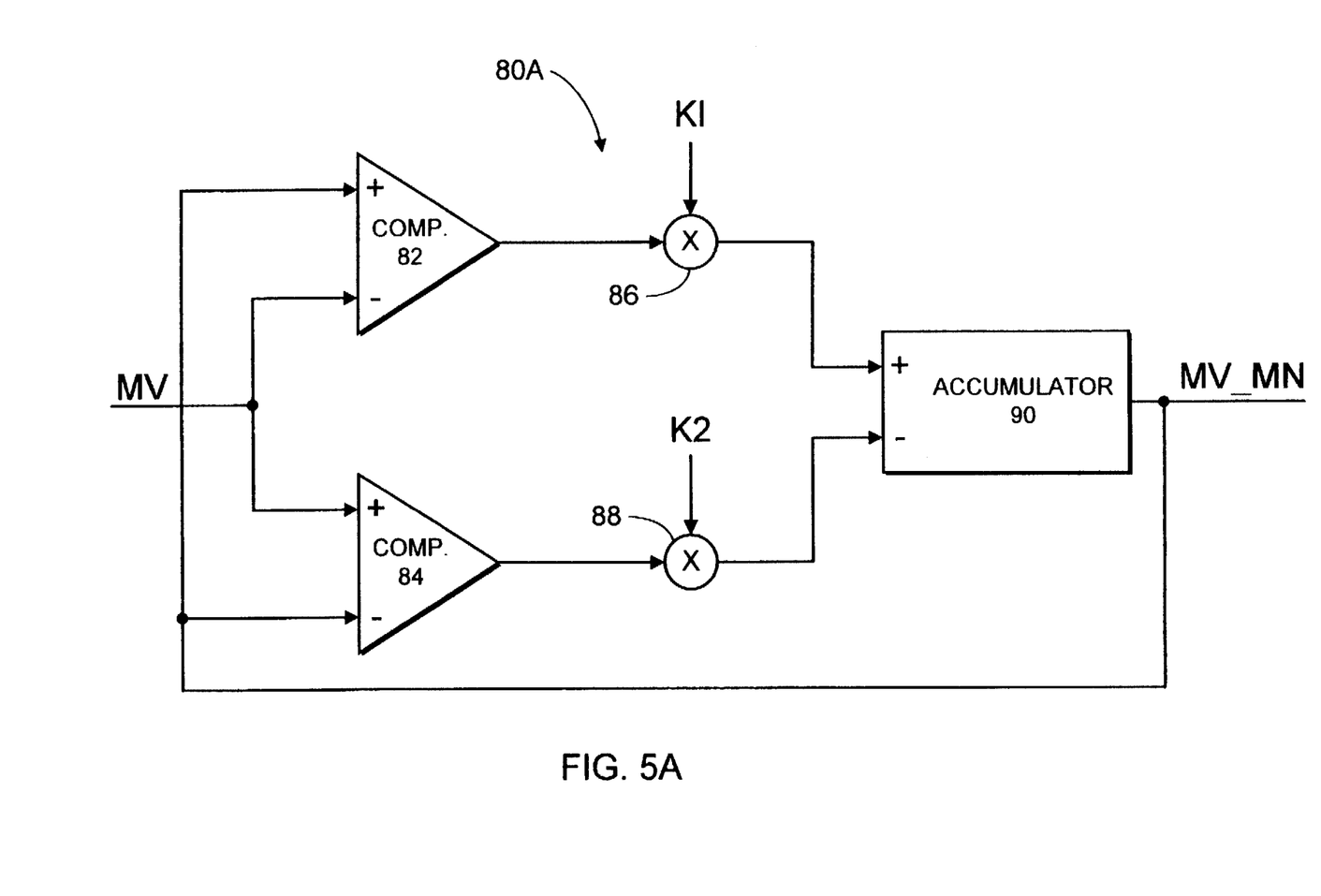
FIG. 5A shows details of a typical low pass filter used in FIG. 5.

After implantation the MV measurements are also fed from circuit 70 to a plurality of low pass filters 80A, 80B and 80C. These filters preferably have a constant rising and falling slew rate matching the change in the average activity of the patient. A typical time constant for these rates is about a month. The details of the low pass filter 80A are shown in FIG. 5A. The filter includes two comparators 82, 84, an adder 86, a subtractor 88 and an accumulator 90. The comparator 82 receives as an input the current MV parameter and a threshold level or constant T1. This comparator generates an output if the parameter MV exceeds T1. Similarly comparator 84 receives the MV parameter and another threshold level T2. Comparator 84 generates an output if the MV parameter is below T2. It should be emphasized that while in prior art pacemakers, a $^{\Delta}$MV parameter is used as the control parameter which is the difference between the actual MV parameter and a baseline obtained from a long term filter, in the present invention the actual or instantaneous MV parameter is used. An output from comparator 82 activates adder 86. When activated, the adder 86 take the contents of accumulator 90 and adds thereto a small constant K1. The resulting sum is stored in the accumulator 90.

Similarly an output from comparator 84 activates the subtractor 88. The subtractor 88 takes contents of accumulator 90 and subtracts from it the constant K2. The difference is stored back into the accumulator 90. The resulting output of the accumulator is the accumulative percentile of the parameter MV. This percentile is determined by the ratio of K1/K2. As previously mentioned, filter 80A is provided to generate the parameter MV_MIN which corresponds to the 10% cumulative percentile of MV as shown in FIG. 8. Therefore for filter 80A, the ratio of K1/K2=0.1. The other filters 80B, 80C are identical to 80A except for the ratio of the threshold levels for the comparators. These ratios are, respectively, 90% and 99.7%.

The outputs of the filters 80A–80C are provided to the mapping circuit 74.

For a pre-selected training period, the mapping circuit 70 generates an MIR parameter for each MV measurement based on the critical profile derived as described above. During this time, equivalent to the time constant of the filters 80A–80C, the filter accumulators 90 collect MV data specific to the patient. At the end of the training period, sufficient data has been collected to define patient specific values for parameters MV_MIN, MV_LE, and MV_MAX. These new parameters are used to generate a new profile curve. Thereafter, the profile curve is recalculated at regular intervals using the parameters for the filters 80A–80C.

Figure 10:
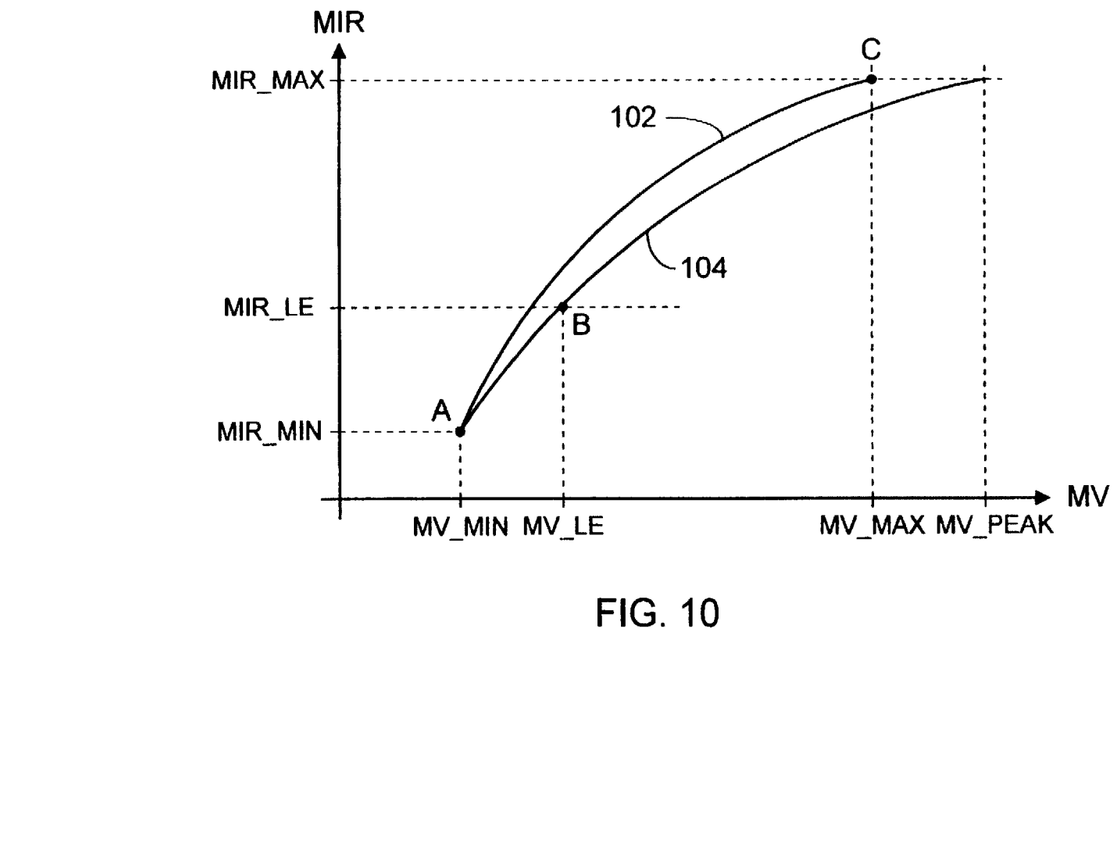
FIG. 10 shows how a mapping profile is generated by the invention.

The three filters thus generate the parameters MV_MIN, MV_LE, and MV_MAX. The corresponding values MIR_MIN, MIR_LE and MIR_MAX are either provided by the attending physician or known from statistical data and stored in memory 78. This data define three sets of points identified as A, B and C on FIG. 10. However, since only two points are needed to define the profile, the third point is used for cross-check. Thus, as shown in FIG. 10, a first curve 102 is defined by points A and C; and a second curve 104 is defined by points A and B.

The mapping circuit 76 uses the lower of these curves, i.e., curve 104 as the mapping profile. The intersection of these curves with MIR_MAX defines MV_PEAK.

In this manner, the mapping circuit is constantly updated and dynamically changed to conform to the status of the patient.

This operation automatically compensates for physiological and pathological changes of the patient.

The invention described herein may be used in a pacemaker in which MV_PEAK is determined by a scale factor applied to the minute volume signal rather than being determined directly by the profile curve. In this case, an error signal may be derived from the difference between the actual value of MV_PEAK and the value of MV_PEAK determined by the profile curve, thus providing a closed loop system. For this type of control, the times and magnitudes of the gain adjustments must be carefully selected to insure stability, cross check for the heart rate derived from the minute volume measurements. In this case, an error signal may be derived from the differences between the two sensor outputs, thus providing a closed loop control system. For this type of control, the times when any gain adjustments must be carefully selected to insure stability.

Although the invention has been described with reference to a preferred embodiment, it is to be understood that this embodiment is merely illustrative of the application of the principles of the invention. Accordingly, the embodiment described in particular should be considered exemplary, not limiting, with respect to the following claims.

We claim:

1. An implantable pacemaker for assisting the cardiac function of a patient comprising:

pulse generating means for generating pacing pulses in accordance with a metabolic rate parameter;

sensing means for sensing an instantaneous rate control parameter in said patient;

means for generating a cumulative rate control parameter by monitoring said instantaneous rate control parameter over an extended time over of at least a day;

determining means for determining a set of physical activity parameters from said cumulative rate control parameter;

mapping means receiving said physical activity parameters and generating in response a mapping profile, said profile being defined by a predetermined arithmetic function relating physical activity to said metabolic rate parameter; and conversion means for converting said instantaneous rate control parameter into said metabolic parameter using said mapping profile.

2. The pacemaker of claim 1 wherein said instantaneous control rate parameter comprises a minute volume.

3. The pacemaker of claim 1 wherein said metabolic parameter comprises a metabolic indicated rate.

4. The pacemaker of claim 1 wherein said mapping means includes defining means for defining a curve from said physical activity parameters using said predetermined arithmetic function.

5. The pacemaker of claim 1 wherein said determining means includes calculating means for calculating said set of physical activity parameters by calculating predetermined percentiles of said cumulative control rate parameter, said percentiles being correlated to preselected activity levels of said patient.

6. An implantable pacemaker comprising:

a pacing generator for generating pacing pulses in accordance with a metabolic parameter;

a sensor for sensing physiological characteristics within the patient;

a calculator including a determinating circuit for determining an instantaneous control parameter from said physiological characteristics, a monitor for monitoring said instantaneous parameter over a long time period to determine physical activity parameters related to the physical condition of the patient;

a converter for converting said physical activity parameters into a curve defining a relationship between said instantaneous control parameter and said metabolic parameter with said curve being defined from a predetermined arithmetic function; and a controller for generating for each said instantaneous control parameter a corresponding metabolic parameter from said curve.

7. The pacemaker of claim 6 wherein said control parameter comprises a minute volume.

8. The pacemaker of claim 6 further comprising a memory for storing generalized cardiac data derived from a patient population, wherein said curve is determined based on said data.

9. The pacemaker of claim 6 wherein said metabolic parameter comprises a metabolic indicated rate.

10. The pacemaker of claim 6 wherein said determinating circuit determines at least two athletic activity parameters defining the instantaneous control parameter corresponding to sleep conditions, light exercise, and peak exercise.

11. The pacemaker of claim 10 wherein two activity parameters define said curve.

12. The pacemaker of claim 11 wherein said determinating circuit determines two curves corresponding to two sets of said athletic parameters, and then chooses one of said curves, the selected curve having a lower peak metabolic parameter.

13. The pacemaker of claim 6 wherein said determinating circuit includes an accumulator for generating a cumulative control parameter from said instantaneous parameter and said physical activity parameters are determined from preselected percentile values of said cumulative control parameter.

14. The pacemaker of claim 13 wherein said curve comprises a monotonic curve.

15. The pacemaker of claim 14 wherein said curve comprises a logarithmic curve.

16. The pacemaker of claim 9 wherein said curve comprises a mapping curve relating a minute volume as said metabolic parameter to a metabolic indicated pacing rate as said instantaneous control parameter.

17. The pacemaker of claim 16 wherein said converter selects said curve with said metabolic indicating pacing rate increasing when said metabolic parameter increases.

* * * * *